(12) United States Patent
Chung et al.

(10) Patent No.: US 12,064,762 B2
(45) Date of Patent: Aug. 20, 2024

(54) GENE AMPLIFICATION APPARATUS

(71) Applicant: ELECTRONICS AND TELECOMMUNICATIONS RESEARCH INSTITUTE, Daejeon (KR)

(72) Inventors: Kwang Hyo Chung, Daejeon (KR); Hyo Jeong An, Daejeon (KR); Han Young Yu, Daejeon (KR); Yo Han Choi, Daejeon (KR)

(73) Assignee: ELECTRONICS AND TELECOMMUNICATIONS RESEARCH INSTITUTE, Deajeon (KR)

( * ) Notice: Subject to any disclaimer, the term of this patent is extended or adjusted under 35 U.S.C. 154(b) by 190 days.

(21) Appl. No.: 17/665,248

(22) Filed: Feb. 4, 2022

(65) Prior Publication Data

US 2023/0061904 A1    Mar. 2, 2023

(30) Foreign Application Priority Data

Aug. 31, 2021    (KR) ........................ 10-2021-0115714

(51) Int. Cl.
  *B01L 3/00*    (2006.01)
  *B01L 7/00*    (2006.01)
  *C12Q 1/686*   (2018.01)

(52) U.S. Cl.
  CPC ........... *B01L 3/502715* (2013.01); *B01L 7/52* (2013.01); *B01L 2300/0663* (2013.01);
  (Continued)

(58) Field of Classification Search
  CPC ....... B01L 2200/147; B01L 2300/0663; B01L 2300/0819; B01L 2300/0832;
  (Continued)

(56) References Cited

U.S. PATENT DOCUMENTS 7,398,015 B2    7/2008  Chung
8,735,103 B2    5/2014  Chung
(Continued)

FOREIGN PATENT DOCUMENTS

KR    10-0758273 B    9/2007
KR    10-2043103 B    11/2019

OTHER PUBLICATIONS

Jae Hwan Jung, et el., "Ultrafast Rotary PCR system for multiple influenza viral RNA detection", Lab on a Chip, Mar. 22, 2012, pp. 1598-1600, vol. 12(9).

*Primary Examiner* — Christine T Mui
*Assistant Examiner* — Jonathan Bortoli

(57) ABSTRACT

Provided is a gene amplification apparatus. The gene amplification apparatus includes a supply roller, a roll-type film chip which has a plurality of polymerase chain reaction (PCR) chambers, with which PCR samples are filled, and is wound around the supply roller, a heating roller configured to rotate after being pressed against the film chip and then induce a PCR, a plurality of heating blocks which are disposed on a circumferential surface of the heating roller at preset intervals and brought into contact with the film chip, and a discarding roller configured to discard the film chip which passes the heating roller and on which the PCR is performed.

10 Claims, 14 Drawing Sheets

(52) U.S. Cl.
CPC ... *B01L 2300/0819* (2013.01); *B01L 2300/12* (2013.01); *B01L 2300/1805* (2013.01); *C12Q 1/686* (2013.01)

(58) Field of Classification Search
CPC ......... B01L 2300/0887; B01L 2300/12; B01L 2300/123; B01L 2300/1805; B01L 3/502715; B01L 7/52; B01L 7/5255; B01L 9/527; C12Q 1/686
See application file for complete search history.

(56) References Cited

U.S. PATENT DOCUMENTS

| | | |
|---|---|---|
| 11,193,098 B2 | 12/2021 | Kim |
| 2004/0076996 A1* | 4/2004 | Kondo ................ C12Q 1/6837 435/6.11 |
| 2005/0221358 A1* | 10/2005 | Carrillo ................ G01N 21/648 435/6.16 |
| 2008/0064086 A1 | 3/2008 | Lee et al. |
| 2010/0267127 A1 | 10/2010 | Chung |
| 2015/0224504 A1* | 8/2015 | Anderson ............. B32B 37/182 156/146 |

\* cited by examiner

B-B'

C-C'

GENE AMPLIFICATION APPARATUS

CROSS-REFERENCE TO RELATED APPLICATION

This application claims priority to and the benefit of Korean Patent Application No. 10-2021-0115714, filed on Aug. 31, 2021, the disclosure of which is incorporated herein by reference in its entirety.

BACKGROUND

1. Field of the Invention

The present invention relates to a gene amplification apparatus.

2. Discussion of Related Art

Organisms possessing nucleic acids have species- or individual-specific gene sequences. A method of examining a gene for discriminating an organism through analysis of a specific gene among gene sequences has been developed.

In general, genes are present in an analysis sample at an extremely low concentration, and an amplification process is generally performed for gene analysis.

As a representative method for gene amplification, there is polymerase chain reaction (hereinafter, referred to as "PCR"). PCR technology is a technology for amplifying a gene having a specific sequence, which is an amplification target, by inducing a chain catalytic reaction by applying thermal cycling that gives two to three stages of temperature changes to a gene amplification sample (which is prepared by mixing a deoxyribonucleic acid (DNA) template, a primer, a polymerase, a deoxyribonucleotide triphosphate (dNTP), a buffer, etc.).

More specifically, the PCR technology is a method of allowing the number of genes to be doubled per cycle through thermal cycling composed of a denaturation process (90 to 98 degrees) of separating a DNA double helix, an annealing process (50 to 65 degrees) of controlling a primer to find a complementary pair of DNA templates, and an extension process (68 to 75 degrees) of growing DNA.

Recently, several methods for thermal cycling have been developed for a change in temperature of PCR amplification samples, but when a method of periodically replacing and applying heating sources that are maintained at different constant temperatures to a sample stopped in a small container is used, the temperature may be simply controlled.

Further, in the above method, a thermal weight of the heating source may be made relatively larger than that of a sample container so that a temperature change time of the sample may be shortened, but there was a problem in that a tool that moves the heating source and control thereof are unavoidable and the heating source should be stably pressed against the sample container for each movement of the sample container.

SUMMARY OF THE INVENTION

The present invention is directed to solving the above-described problems, and providing a gene amplification apparatus capable of simplifying driving a heating source by arranging the heating source on a surface of a roller and solving a problem of a heating source pressed against the conventional sample container.

Objects of the present invention are not limited to the above-described object and other objects that are not described may be clearly understood by those skilled in the art from the following descriptions.

According to an aspect of the present invention, there is provided a gene amplification apparatus including a supply roller, a roll-type film chip which has a plurality of polymerase chain reaction (PCR) chambers, with which PCR samples are filled, and is wound around the supply roller, a heating roller configured to rotate after being pressed against the film chip and then induce a PCR, a plurality of heating blocks which are disposed on a circumferential surface of the heating roller at preset intervals and brought into contact with the film chip, and a discarding roller configured to discard the film chip which passes the heating roller and on which the PCR is performed.

The heating block may be sequentially brought into contact with the film chip by rotation of the heating roller and may induce gene amplification of the PCR sample present in the film chip.

The plurality of heating blocks may be disposed on an outer peripheral surface of the heating roller at regular intervals and may be constantly maintained at different temperatures for denaturation, annealing, and extension, which are steps of PCR thermal cycling.

The heating roller may have a hollow shape and may be made of a heat insulating material so that the plurality of heating blocks disposed on the circumferential surface thereof are maintained at different temperatures.

The heating roller may include an external heating roller structure having a hollow shape and having a curvature corresponding to the heating block, and a hole configured to communicate an inner space of the external heating roller structure with the outside.

The plurality of heating blocks may be disposed on a surface of the external heating roller structure so as to be maintained at different temperatures.

The heating roller may be disposed between the supply roller and the discarding roller so that some sections of the film chip in contact with the heating roller are pressed against the heating roller with a step difference.

The film chip may be temporarily stopped while being moved toward the discarding roller so that the PCR chamber is filled with the PCR sample.

The PCR chamber may be blocked from outside air after the film chip is aligned with an upper contact surface of the heating roller.

A connection channel and a sample inlet may form one conduit so that the PCR chamber is filled with the PCR sample, and when the PCR chamber is filled with the PCR sample using the connection channel through the sample inlet, a separate elastically deformable body may block the sample inlet from the outside air.

The film chip may be formed by laminating a plurality of films manufactured with the same pattern.

According to another aspect of the present invention, there is provided a gene amplification apparatus including a roll-type film chip having a plurality of PCR chambers which are allowed to be filled with PCR samples, a heating roller configured to rotate after being pressed against the film chip and then induce a PCR, a plurality of heating blocks which are disposed on a circumferential surface of the heating roller at preset intervals and brought into contact with the film chip, a temperature sensor configured to detect a temperature of the heating block, a heater configured to maintain the heating block at a constant temperature, and a controller configured to receive a current temperature value of the heating block from the temperature sensor, compare the current temperature value with a reference temperature value, and then control the heater according to a result of the comparison.

The controller may rotate and temporarily stop the heating roller to allow the heating blocks to be sequentially brought into contact with the film chip and induce gene amplification of the PCR sample present in the film chip.

A slip ring for preventing a wire between the heater and the temperature sensor from being twisted may be provided in an inner space of the heating roller.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Advantages and features of the present invention and methods of achieving the same will be clearly understood with reference to the accompanying drawings and embodiments described in detail below. However, the present invention is not limited to the embodiments to be disclosed below and may be implemented in various different forms. The following embodiments are merely provided to easily inform those skilled in the art of the objects, configuration, and effects of the present invention. The scope of the present invention is defined by the appended claims. Meanwhile, the terms used herein are provided only to describe the embodiments of the present invention and not for purposes of limitation. In this specification, the singular forms include the plural forms unless the context clearly indicates otherwise. It will be understood that the terms "comprise" and/or "comprising," when used herein, specify some stated components, steps, operations and/or elements but do not preclude the presence or addition of one or more other components, steps, operations and/or elements. As used herein, the term "and/or" includes any and all combinations of one or more of the associated listed items.

Hereinafter, exemplary embodiments of the present invention will be described in detail with reference to the accompanying drawings.

In the present invention, an apparatus and method in which, by arranging two or three heating sources that are maintained at different constant temperatures on a surface of a roller, allowing a flexible film chip to be pressed against the surface of the roller, and then continuously rotating the roller in a predetermined direction, thermal cycling is performed on a gene amplification sample in the film chip are provided. Further, a method of consecutively performing gene amplification multiple times by consecutively replacing film chips is provided. Hereinafter, the present invention will be described with reference to embodiments.

Figure 1:
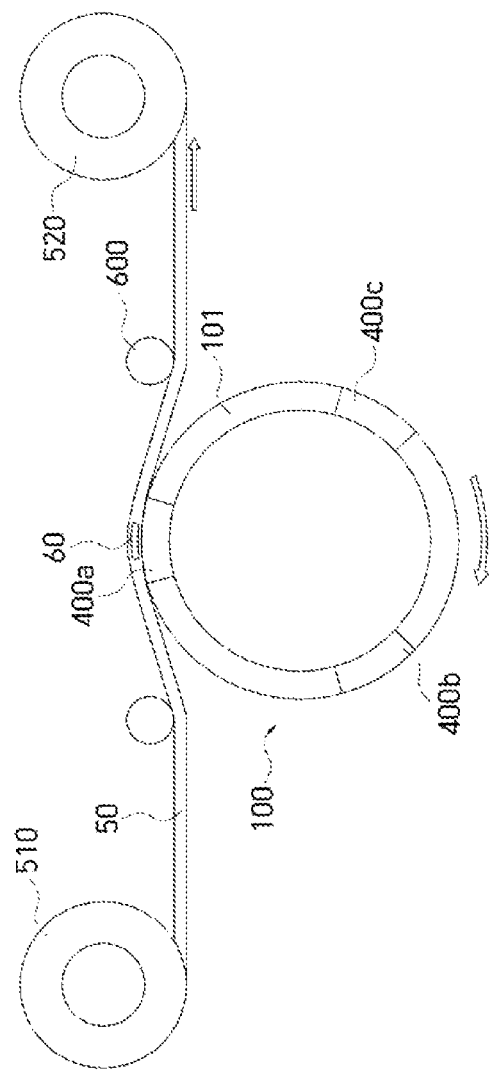
FIG. 1 is an exemplary configuration diagram schematically illustrating a gene amplification apparatus according to an embodiment of the present invention.

FIG. 1 is an exemplary configuration diagram schematically illustrating a gene amplification apparatus according to an embodiment of the present invention.

Referring to FIG. 1, a gene amplification apparatus 10 according to the embodiment of the present invention largely includes a film chip 50, a heating roller 100, and heating blocks 400a, 400b, and 400c.

The film chip 50 is manufactured by laminating flexible films, and a polymerase chain reaction (PCR) chamber 60 is provided inside the film chip 50. The PCR chamber 60 is filled with a PCR sample 910 (see FIG. 3) input from an external unit (e.g., a sample supply unit 900 of FIG. 3).

The film chip 50 is wound around a supply roller 510 in the form of a roll and stored.

In order to perform PCR, the film chip 50 is moved to an upper contact surface of the heating roller 100 and temporarily stopped, and after the performance of the PCR is completed, the film chip 50 is moved to a discarding roller 520 by rotation of the heating roller 100 to be wound around the discarding roller 520 and is discarded. The process in which the film chip 50 is moved is similar to an operation in which a film of a film camera is moved.

The film chip 50 may be pulled and moved to the discarding roller 520 by driving a motor installed in the discarding roller 520, and the PCR chamber 60 in the film chip 50 is moved and controlled to be aligned with the upper contact surface of the heating roller 100 in order to perform PCR.

Through the rotation of the heating roller 100, temperature changes for denaturation, annealing, and expansion for PCR thermal cycling are applied to the PCR sample with which the PCR chamber 60 in the film chip 50 is filled.

The PCR thermal cycling is performed one time whenever the heating roller 100 rotates one time. Generally, the PCR thermal cycling is performed 30 to 40 times. That is, the PCR thermal cycling is completed by the rotation of the heating roller 100 30 to 40 times in a state in which the film chip 50 is stopped.

In order to strongly press the film chip 50 against the heating roller 100, in other words, in order to maintain the film chip 50 pulled by the motor installed in the discarding roller 520 taut, a torque motor (not illustrated) for applying a constant torque resistance in a direction opposite to a moving direction of the film chip 50 may be installed in the supply roller 510, or a powder brake (not illustrated) capable of resisting the movement of the film chip 50 until a predetermined force or more is applied may be additionally installed.

The heating roller 100 has a structure including an external heating roller structure 101 having a circular roller shape, and the heating blocks 400a, 400b, and 400c manufactured to match a curvature of the external heating roller structure 101 may be inserted into a circumferential surface of the heating roller 100 to form a circular roller shape. In this case, according to needs such as reducing friction with the film chip 50 and the like, the heating blocks 400a, 400b, and 400c may slightly protrude from the circumferential surface of the heating roller 100.

A protruding structure may be formed on a part of a surface of the external heating roller structure 101 or a hole connected from an inner space 102 of the heating roller 100 to the outside may be formed so that a specific operation may be additionally applied to a bottom surface of the film chip 50, which is brought into contact with the heating roller 100.

For example, due to the protruding structure, a force may be applied to a structure such as tape or the like additionally formed on the bottom surface of the film chip 50, and a knife-shaped protruding structure may be formed to apply deformation to the film chip 50. Further, an air flow for cooling may be applied to the bottom surface of the film chip 50 through the hole of the external heating roller structure 101, and light may be incident on the film chip 50 through the hole or leaked external light may be received by the film chip 50.

The external heating roller structure 101 may be manufactured using a heat insulating material for thermal isolation between the plurality of heating blocks 400a, 400b, and 400c. Here, the heat insulating material may include insulating plastic, styrofoam, urethane foam, glass fiber, a fiber insulating material, a heat reflective insulating material, a vacuum insulating material, or the like.

The plurality of heating blocks 400a, 400b, and 400c may be disposed on the surface of the external heating roller structure 101 to be maintained at different temperatures.

The heating blocks 400a, 400b, and 400c may be disposed at regular intervals according to the number thereof for rotation control and simplification of design.

For example, when three heating blocks 400a, 400b, and 400c are formed, the heating blocks 400a, 400b, and 400c may be disposed at intervals of 120 degrees. The number of heating blocks 400a, 400b, and 400c may be at least two or three depending on a temperature cycling method of PCR.

The heating blocks 400a, 400b, and 400c may be added to perform a function of applying different temperatures for gene analysis other than PCR, such as gene pretreatment, reverse transcription, or the like. Further, n heating blocks 400a, 400b, or 400c having the same temperature may be disposed to overlap with each other according to design requirements.

The temperatures of the heating blocks 400a, 400b, and 400c are each maintained constantly for denaturation (corresponding heating block 400a), annealing (corresponding heating block 400b), and extension (corresponding heating block 400c) which are steps of PCR thermal cycling, and the heating roller 100 is rotated in a clockwise direction.

On the other hand, the heating blocks 400a, 400b, and 400c may be manufactured of a metal material (e.g., aluminum, an aluminum alloy, copper, a copper alloy, etc.) with high thermal conductivity to maintain a constant temperature. The heating blocks 400a, 400b, and 400c may be manufactured in a size having a relatively larger heat capacity than a heating target such as a contact surface of the film chip 50, the sample in the PCR chamber 60, or the like.

Outer surfaces of the heating blocks 400a, 400b, and 400c, which are brought into contact with the film chip 50, are mirror-finished through surface polishing so that stable contact and heat transmission are possible.

For stable heat transmission to the film chip 50 and smooth rotation of the heating roller 100, a lubricant, thermal grease, oil, or the like may be applied to the outer surfaces of the heating blocks 400a, 400b, and 400c.

The gene amplification apparatus 10 may additionally include guide rollers 600.

The guide roller 600 serves to allow the film chip 50 to be brought into good contact with the surface of the heating roller 100 with a constant curvature.

The guide roller 600 may include protrusion structures (not illustrated) corresponding to punching holes at regular intervals in the film chip like a film of a film camera so that the film chip 50 and the heating roller 100 are stably pressed against each other.

Figure 2:
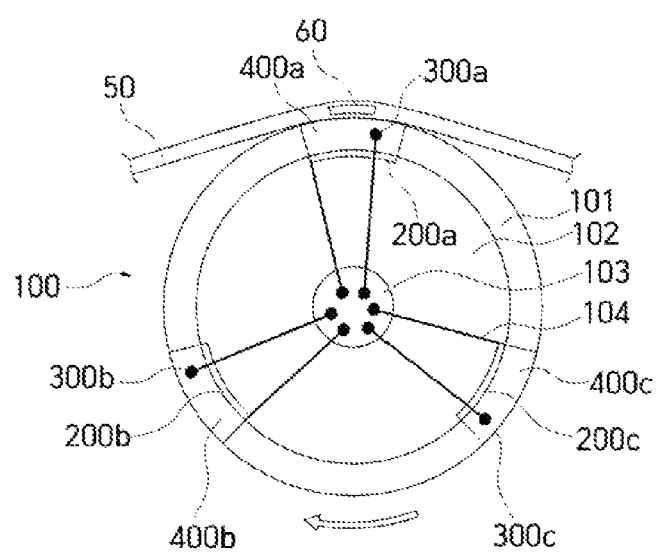
FIG. 2 is an exemplary diagram illustrating a structure of a heating roller according to an embodiment of the present invention.

FIG. 2 is an exemplary diagram illustrating a structure of a heating roller according to an embodiment of the present invention.

Referring to FIG. 2, a heating roller 100 includes heaters 200a, 200b, and 200c and temperature sensors 300a, 300b, and 300c.

The heaters 200a, 200b, and 200c are disposed inside heating blocks 400a, 400b, and 400c, respectively, to maintain the heating blocks 400a, 400b, and 400c at a constant temperature. The heaters 200a, 200b, and 200c may include film heaters, flexible printed circuit board (FPCB) heaters, thermoelectric elements (TECs), or the like.

The temperature sensors 300a, 300b, and 300c are disposed in the heating blocks 400a, 400b, and 400c to detect a temperature of a corresponding section.

The temperature sensors 300a, 300b, and 300c may include thermocouples, resistance temperature detectors (RTDs), thermistors, or the like.

The heaters 200a, 200b, and 200c and the temperature sensors 300a, 300b, and 300c are connected to a controller (not illustrated) through wires 104. The controller may receive temperature values of the heating blocks 400a, 400b, and 400c from the temperature sensors 300a, 300b, and 300c and control the heaters 200a, 200b, and 200c so as to maintain the temperature values at a reference temperature value.

A slip ring 103 may be installed between each of the controller and the heaters 200a, 200b, and 200c and each of the temperature sensors 300a, 300b, and 300c so as to prevent the occurrence of twisting caused by the rotation of the heating roller 100.

The external heating roller structure 101 may be formed to have a minimum thickness for thermal insulation and, accordingly, an inner space 102 of the heating roller 100 may become a cavity. In the inner space 102 of the heating roller 100, an optical part, an air pump, and the like may be additionally installed according to needs such as signal measurement, cooling of the film chip 50, and the like.

Figure 3:
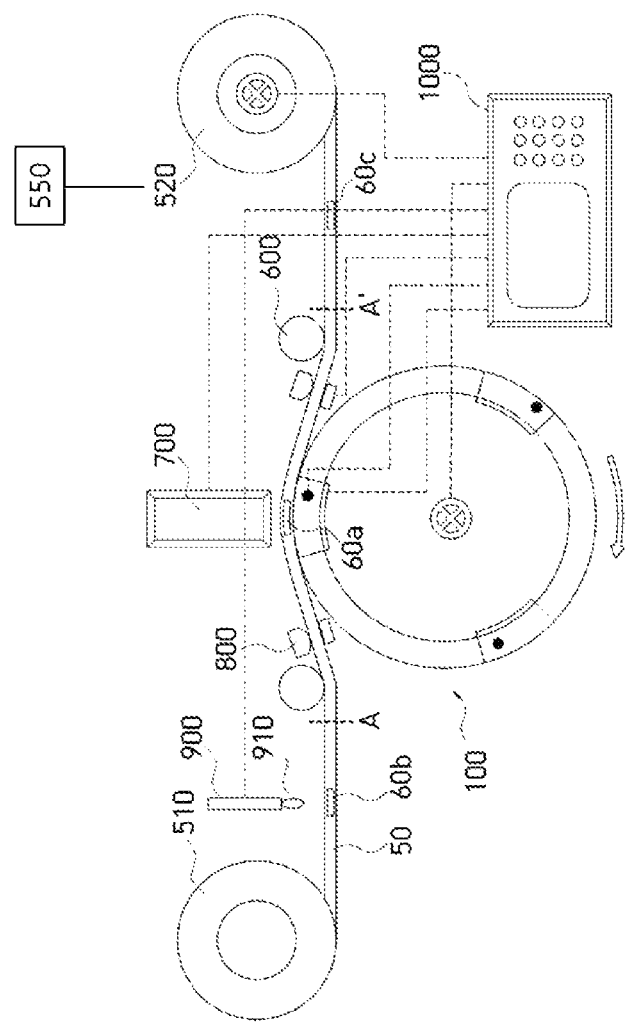
FIG. 3 is an exemplary configuration diagram illustrating an operational relationship between components of a gene amplification apparatus according to another embodiment of the present invention.

FIG. 3 is an exemplary configuration diagram illustrating a gene amplification apparatus according to another embodiment of the present invention.

A gene amplification apparatus 10' of FIG. 3 may have additional functions such as thermal control, rotation control, film chip sealing, signal measurement, sample supply, and the like in addition to the functions of the components of the gene amplification apparatus 10 of FIGS. 1 and 2.

A plurality of film chips 50 are manufactured with the same pattern (wherein line A-A' exemplifies one pattern among the same patterns) and are wound around a supply roller 510 and stored.

In order to perform PCR, when the film chip 50 is moved from the supply roller 510 to a discarding roller 520 by driving a discarding roller motor 550, PCR chambers 60 in the film chip 50 may be aligned on an upper contact surface of a heating roller 100.

In the gene amplification apparatus 10', after the film chip 50 is temporarily stopped while the film chip 50 is moved to the discarding roller 520, PCR chambers 60a, 60b, and 60c may be filled with PCR samples 910 provided from a sample supply unit 900.

The PCR chambers 60a, 60b, and 60c should be blocked from outside air after the film chip 50 is moved and aligned on the upper contact surface of the heating roller 100. This is to prevent the formation of bubbles that may occur while PCR in which a high-temperature heat source is applied is performed in the PCR sample 910 and prevent heat loss due to evaporation. Sealing mechanisms 800 block the PCR chambers 60a, 60b, and 60c from the outside air.

By rotation of the heating roller 100, the plurality of heating blocks 400a, 400b, and 400c are sequentially brought into contact with the film chip 50 so that the temperature of the PCR sample 910 is changed in response to a change in temperature of the heating blocks 400a, 400b, and 400c. The PCR is performed through the above process.

The rotation of the heating roller 100 may be rapidly performed for replacement of the heating blocks 400a, 400b, and 400c in contact with the film chip 50, and the heating roller 100 may be stopped for heat transmission to the PCR chambers 60a, 60b, and 60c for a predetermined period of time and then may be replaced with a next heating block by a rotational movement (e.g., 60a→60b).

By sequential rotation of the heating roller 100, gene amplification may be performed on the PCR samples 910 in the PCR chambers 60a, 60b, and 60c, and a signal measuring unit 700 may be installed to measure an amount of gene amplification.

Signal measurement of the signal measuring unit 700 may be performed in real time while the heating roller 100 is rotated or may be performed after the PCR is completed. Here, for the signal measurement, an optical method may be used for non-contact, and the corresponding signal may have a fluorescence intensity that increases in proportion to PCR.

A controller 1000 may control the entire configuration of the gene amplification apparatus 10' and allow the control status to be displayed on a separate screen (e.g., a liquid-crystal display (LCD) or the like).

When a corresponding component for the purpose such as gene extraction or the like for gene analysis is required, the component may be added to the gene amplification apparatus 10' according to the purpose. For example, components for applying electrical and magnetic external forces and a component for extracting an electrical signal may be separately added to the gene amplification apparatus 10'.

Figure 4:
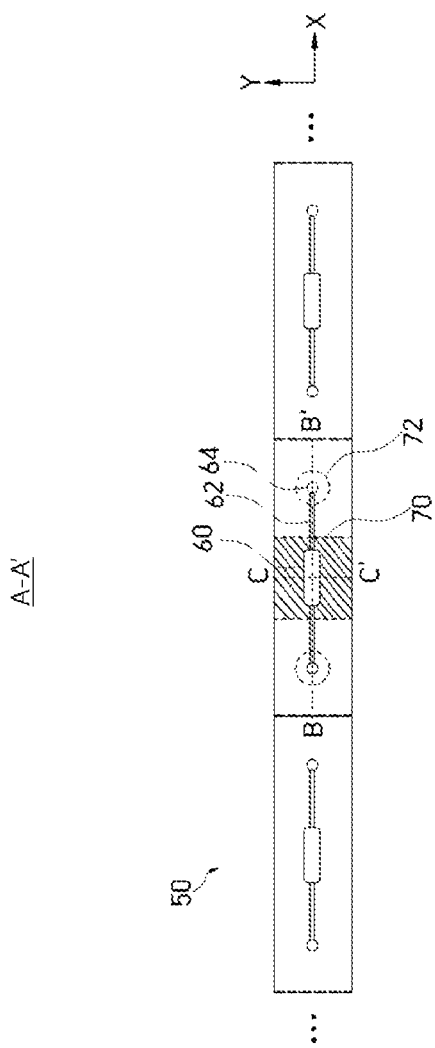
FIG. 4 is a cross-sectional view taken along line A-A' illustrated in FIG. 3.
Figure 5:
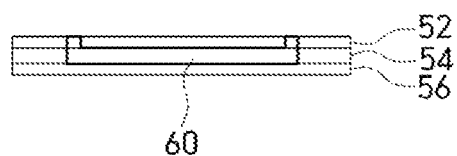
FIG. 5 is a cross-sectional view taken along line B-B' illustrated in FIG. 4.
Figure 5:
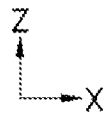
Figure 6:
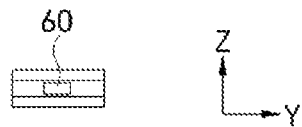
FIG. 6 is a cross-sectional view taken along line C-C' illustrated in FIG. 4.

FIGS. 4 to 6 are exemplary diagrams illustrating in detail the configuration of the film chip of the present invention.

When it is assumed that the center of the PCR chamber 60 of the film chip 50 is set as the origin, FIG. 4 is a plan view (x-y plane) of the film chip 50, FIG. 5 is a cross-sectional view (x-z plane) in a longitudinal direction (x-axis, line B-B') of the film chip 50, and FIG. 6 is a cross-sectional view (y-z plane) in a width direction (y-axis, line C-C') of the film chip 50.

Referring to FIG. 4, a plurality of film chips 50 may be manufactured with the same pattern (line A-A' is one pattern area of the same pattern) and used. In this case, as an example in which one PCR chamber 60 is formed in one pattern, a sample inlet 64 and a connection channel 62 may be formed to fill the PCR chamber 60 with a sample.

The PCR chamber 60 may be filled with a PCR sample, which is introduced into one side of the sample inlet 64, due to a capillary force, and in this case, the other side of the sample inlet 64 may become an outlet through which air is discharged.

A heating part 70 of FIG. 4 is a contact surface, at which the film chip 50 is pressed against the heating block, and is a virtual surface through which the heat of the heating block is transmitted to the PCR chamber 60 by being brought into contact with the film chip 50.

The heating part 70 may be formed to have a size greater than a width and length of the PCR chamber 60 so that the heat is stably transmitted to the sample in the PCR chamber 60. A sealing part 72 is a virtual surface (part) at which the sealing mechanism 800 and the film chip 50 are brought into contact with each other.

Referring to FIGS. 5 and 6, the film chip is formed by laminating a plurality of films composed of an upper layer 52, an intermediate layer 54, and a lower layer 56.

The sample inlet 64 is formed in the upper layer 52.

The connection channel 62 and the PCR chamber 60 may be formed in the intermediate layer 54.

The lower layer 56 may be manufactured as a substrate on which no pattern is formed. The plurality of laminated films may be stably bonded by a method such as thermal bonding, adhesive bonding, thermal melt film bonding, or the like. As the corresponding film, a polymer material such as polyethylene terephthalate (PET), polycarbonate (PC), or a cyclic olefin copolymer (COC) or a metal thin film may be used, and the corresponding film may be made of a material that does not deform at the temperatures for PCR. A thickness of the film of the lower layer 56 may be in the range of 10 to 100 microns for rapid heat transmission.

After the film chip 50 is formed by laminating the plurality of films, inner wall surfaces of the PCR chamber 60, the connection channel 62, and the sample inlet 64 may be surface-treated using a method of plasma treatment, chemical treatment, biomaterial application, nanomaterial application, or the like in order to prevent the PCR sample from being adsorbed onto the surface of the film and smoothly introduce the sample.

Further, in the PCR chamber 60, a PCR pre-mix may be dried and stored using a freeze-drying method or the like or nanomaterials capable of enhancing PCR may be stored.

Figure 7:
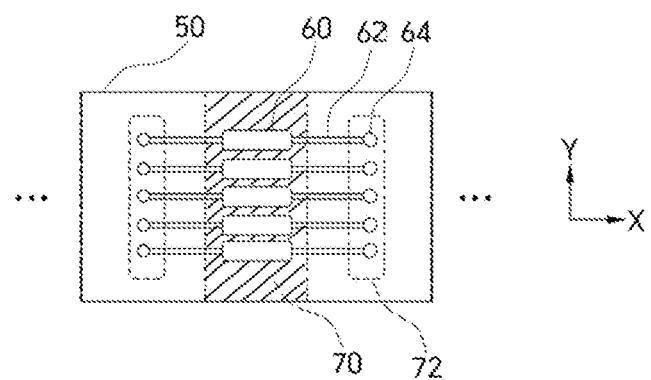
FIGS. 7 to 9 are exemplary diagrams for describing various changes in arrangement of a polymerase chain reaction (PCR) chamber, a connection channel, and a sample inlet in a film chip.
Figure 8:
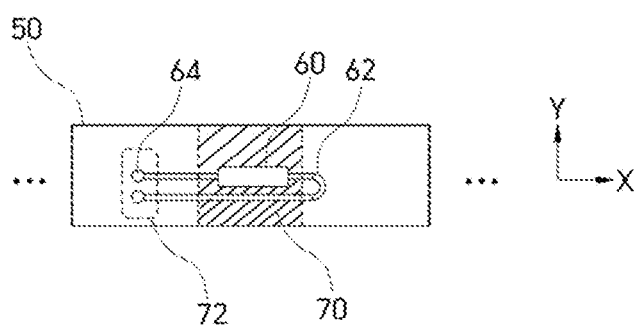
Figure 9:
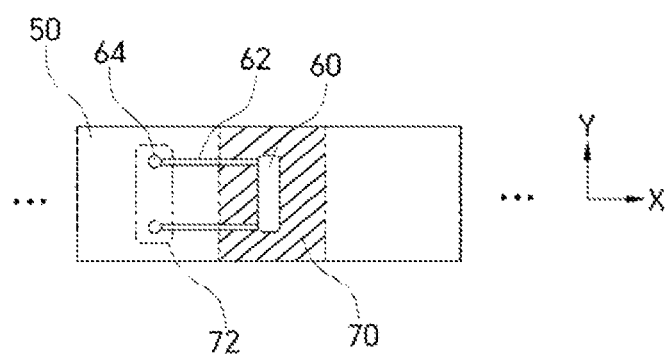

FIGS. 7 to 9 are exemplary diagrams for describing various changes in arrangement of a PCR chamber, a connection channel, and a sample inlet in a film chip.

FIG. 7 illustrates an example in which a plurality of PCR chambers are formed in a width direction (y-axis) in an array. A heating part 70 may be formed to have an area that is shared by the plurality of PCR chambers and a sealing part 72 may also be formed to have an area that is shared by a plurality of sample inlets 64.

FIGS. 8 and 9 illustrate examples in which a connection channel 62 and sample inlets 64 are formed on one side of the PCR chamber 60 in a longitudinal direction (x-axis) so that a sealing part 72 is formed only on one side. In this case, the number of sealing parts may be reduced.

The PCR chamber 60 may be formed to be elongated in the width direction (y-axis) as illustrated in FIG. 8 or may be formed to be elongated in the longitudinal direction (x-axis) as illustrated in FIG. 9. The PCR chamber 60, the connection channel 62, and the sample inlets 64 may be variously changed according to the number of PCR chambers 60, array formation, and a method of installing the sealing part 72.

FIGS. 10A to 14C are exemplary diagrams illustrating a process of forming a sealing part structure.

Figure 10A:
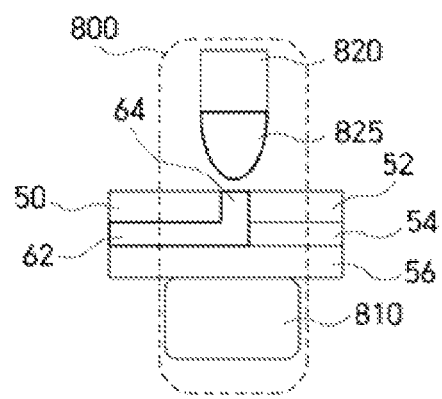
FIGS. 10A to 14C are exemplary diagrams illustrating a process of forming a sealing part structure.
Figure 10B:
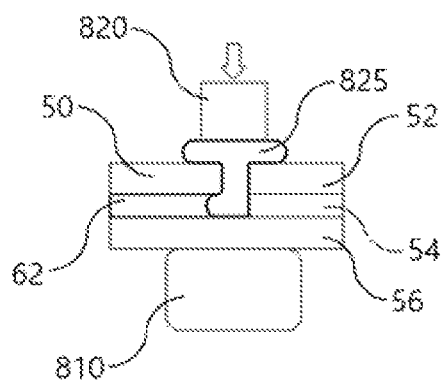

Referring to FIGS. 10A and 10B, a lower sealing structure 810 is disposed in close contact with a downward-facing lower layer 56 of a sample inlet 64 of a film chip 50.

An upper sealing structure 820 is disposed above the lower sealing structure 810 to be spaced apart from the lower sealing structure 810 and is disposed above the sample inlet 64. An elastically deformable body 825 having a downwardly pointed shape is attached to a lower part of the upper sealing structure 820.

When the upper sealing structure 820 is moved toward the film chip 50, the elastically deformable body 825 is deformed to seal the sample inlet 64.

The deformed elastically deformable body 825 may pass through the sample inlet 64 and be introduced to a bottom surface of the intermediate layer 54 of the film chip 50 and to the connection channel 62.

Figure 11A:
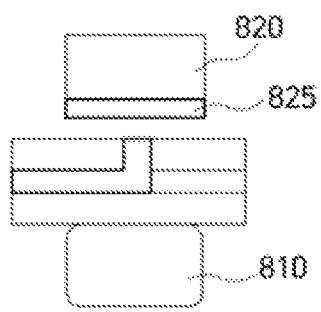
Figure 11B:
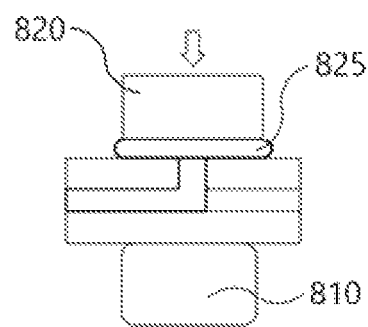

In FIGS. 11A and 11B, an elastically deformable body 825 has a quadrangular cross section.

The elastically deformable body 825 is pressed against an upper layer of a film chip to seal a sample inlet.

Figure 12A:
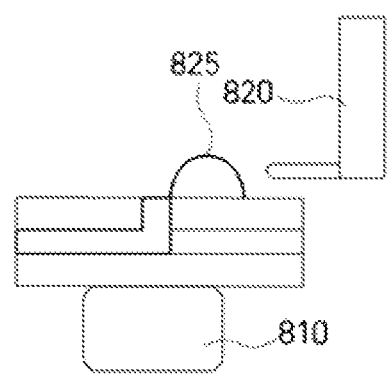
Figure 12B:
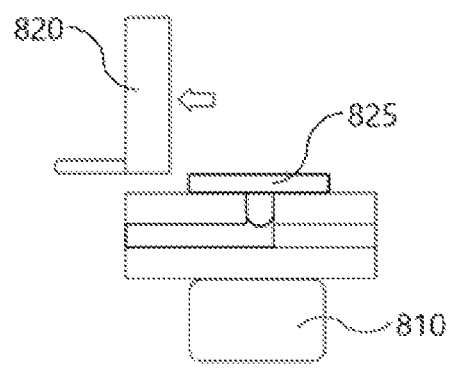

In FIGS. 12A and 12B, an elastically deformable body 825 is installed to be attached to an upper layer of a film chip at one side of a sample inlet. In this example, an upper sealing structure 820 may be moved from one side (right side in the drawing) toward the sample inlet (left side in the drawing) so that the elastically deformable body 825 is pressed and deformed, thereby sealing the sample inlet.

Figure 13A:
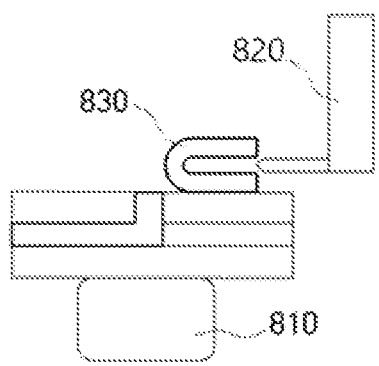
Figure 13B:
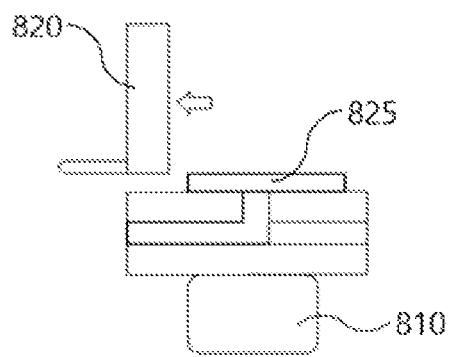

In FIGS. 13A and 13B, a sealing tape 830 is installed to be attached to an upper layer at one side around a sample inlet. In this example, an upper sealing structure 820 may be moved from one side (right side in the drawing) toward the sample inlet (left side in the drawing) so that the sealing tape 830 is pushed to be attached to the sample inlet, thereby sealing the sample inlet.

Figure 14A:
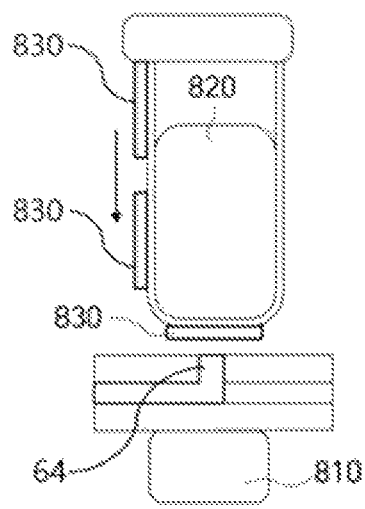
Figure 14B:
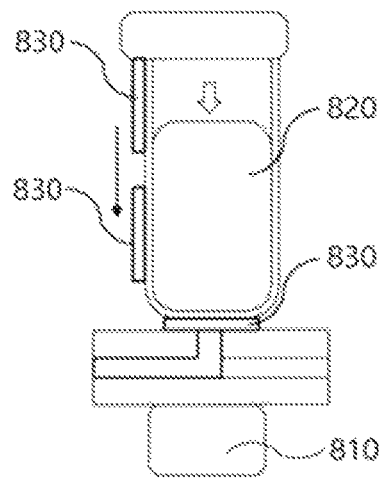
Figure 14C:
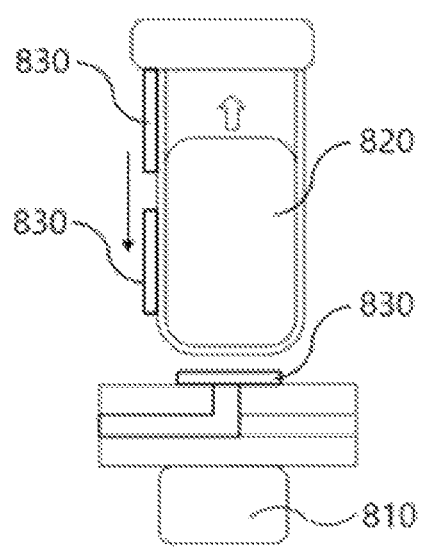

FIGS. 14A to 14C illustrate an example of a structure in which sealing tape 830 is continuously supplied from a side surface of an upper sealing structure 820. For example, in a state in which the sealing tape 830 is disposed to be spaced an interval from a conveyor structure installed on the side surface of the upper sealing structure 820, the sealing tape 830 is temporarily stopped by the upper sealing structure 820 at a position facing a sample inlet 64.

In this case, the sealing tape 830 is attached to be pressed against the sample inlet 64 of the film chip while being moved to the sample inlet 64 by the upper sealing structure 820.

As described above, although various examples of the sealing part structure are described with reference to FIGS. 10A to 14C, other methods of sealing the sample inlet while performing PCR may be applied. As an example of the application, a structure in which a sample inlet is sealed by applying a magnetic force or electric force or a structure in which a sample inlet is sealed by applying heat to a phase change material may be provided.

Figure 15:
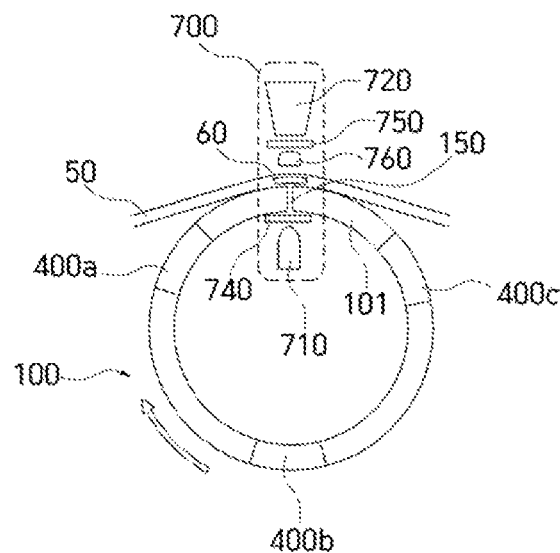
FIGS. 15 and 16 are partial configuration diagrams illustrating a structure of a signal measuring unit.
Figure 16:
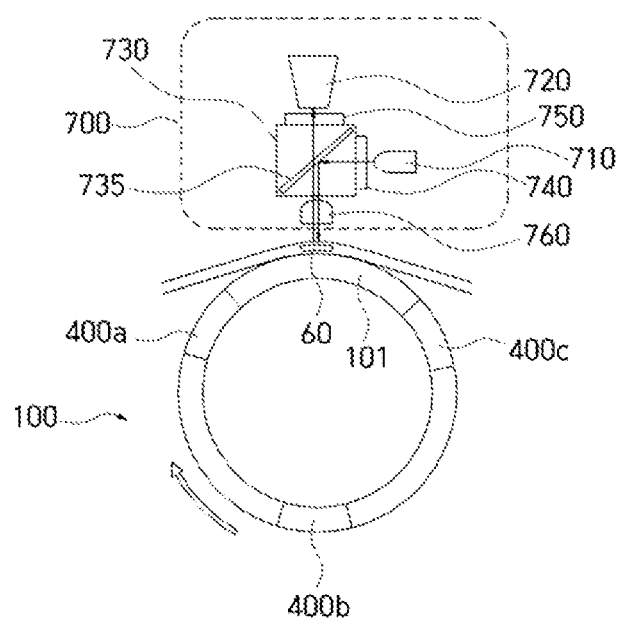

FIGS. 15 and 16 are partial configuration diagrams illustrating a structure of a signal measuring unit.

Referring to FIG. 15, a signal measuring unit 700 may include a light source 710 and a light source filter 740 which are provided in an inner space 102 of a heating roller 100, a hole 150 provided in an external heating roller structure 101, and a light-receiving element 720, a fluorescent filter 750, and a lens 760 which are provided above a film chip 50.

Incident light having a specific wavelength (excitation wavelength) is emitted by filtering light emitted from the light source 710 through the light source filter 740.

Fluorescence of a PCR sample present in a PCR chamber 60 in the film chip 50 is excited through the hole 150, and accordingly, the emitted fluorescence passes through the fluorescent filter 750 and emitting light having a specific wavelength (emission wavelength) is measured by the light-receiving element 720.

When the intensity of the fluorescence is weak, a fluorescence measurement signal of the light-receiving element 720 may be amplified using an additionally installed amplifying circuit (not illustrated).

The light-receiving element 720 may measure an amount of gene amplification performed through PCR by measuring a fluorescence signal in real time through the operation of the signal measuring unit 700 while performing PCR or by measuring the fluorescence after the performance of the PCR is completed.

The hole 150 provided in the external heating roller structure 101 may be provided between a heating block 400c for extension and a heating block 400a for denaturation, and the corresponding signal may be measured after one cycle among a plurality of thermal cycles is completed. The measurement may be stopped for a predetermined period of time so that the hole 150 and the PCR chamber 60 are aligned with each other through the rotation of the heating roller 100.

In the signal measuring unit 700, the light source filter 740 and the fluorescent filter 750 should be applied according to a wavelength suitable for the fluorescence applied to the PCR sample.

In the case in which there are a plurality of applied fluorescences, a structure in which the light source filter 740 and the fluorescent filter 750 are replaced in real time may be applied.

Referring to FIG. 16, a signal measuring unit 700 may be provided above a heating roller 100 and a PCR chamber 60 in a film chip 50. The signal measuring unit 700 may include a light source 710, a light-receiving element 720, a filter cube 730, and a lens 760.

Among the above components, a light source filter 740 and a fluorescent filter 750 are attached to an outer surface of the filter cube 730 in order that incident light and emitting light having specific wavelengths pass therethrough.

A dichroic mirror 735 may be installed inside the filter cube 730 in order to minimize the interference between the incident light and the emitting light.

Incident light having a specific wavelength (excitation wavelength) is emitted by filtering light emitted from the light source 710 through the light source filter 740 and is reflected by the dichroic mirror 735.

The lens 760 excites the fluorescence of the PCR sample 910 (see FIG. 3) present in the PCR chamber 60. In this case, the emitted fluorescence passes through the dichroic mirror 735 and the fluorescent filter 750 and emitting light having a specific wavelength (emission wavelength) is measured by the light-receiving element 720. The corresponding signal may be measured after one cycle among a plurality of thermal cycles is completed.

Meanwhile, a method of driving a gene amplification apparatus may include an operation of inputting a PCR sample into a film chip, an operation of moving the film chip from a supply roller to an upper part of a heating roller, an operation of sealing a sample inlet of the film chip with a sealing mechanism, an operation of performing thermal cycling by rotating the heating roller, an operation of measuring a gene amplification signal while performing the thermal cycling, and an operation of moving the film chip to a discarding roller and discarding the film chip.

According to the present invention, the gene amplification apparatus can simplify the driving of a heating source by arranging the heating source on a surface of a roller, and at the same time, solve a problem of a heating source pressed against the conventional sample container.

In particular, according to the present invention, gene amplification can be performed rapidly and continuously through stably pressing a film chip against a roller and, furthermore, an effect of reducing the cost of a sample container can be obtained.

The present invention is not limited to the above-described embodiments and various modifications can be made within the scope of the technical spirit of the present invention.

REFERENCE NUMERALS 10, 10': GENE AMPLIFICATION APPARATUS
50: FILM CHIP
52: UPPER LAYER
54: INTERMEDIATE LAYER
56: LOWER LAYER
60, 60A, 60B, 60C: PCR CHAMBER
62: CONNECTION CHANNEL
64: SAMPLE INLET
70: HEATING PART
72: SEALING PART
100: HEATING ROLLER
101: EXTERNAL HEATING ROLLER STRUCTURE
102: HEATING ROLLER INNER SPACE
103: SLIP RING
104: WIRE
110: HEATING ROLLER MOTOR
150: HOLE
200: HEATER
300: TEMPERATURE SENSOR
400: HEATING BLOCK
510: SUPPLY ROLLER
520: DISCARDING ROLLER
550: DISCARDING ROLLER MOTOR
600: GUIDE ROLLER
700: SIGNAL MEASURING UNIT
710: LIGHT SOURCE
720: LIGHT-RECEIVING ELEMENT
730: FILTER CUBE
735: DICHROIC MIRROR
740: LIGHT SOURCE FILTER
750: FLUORESCENT FILTER
760: LENS
800: SEALING MECHANISM
810: LOWER SEALING STRUCTURE
820: UPPER SEALING STRUCTURE
825: ELASTICALLY DEFORMABLE BODY
830: SEALING TAPE
900: SAMPLE SUPPLY UNIT
910: PCR SAMPLE
1000: CONTROLLER

What is claimed is:

1. A gene amplification apparatus comprising:
a supply roller;
a film chip which has a plurality of polymerase chain reaction (PCR) chambers configured to accept, PCR samples, and is wound around the supply roller;
a heating roller configured to rotate after being pressed against the film chip and then induce one or more polymerase chain reactions;
a plurality of heating blocks disposed on a circumferential surface of the heating roller at preset intervals wherein the plurality of heating blocks are configured to contact the film chip as the film chip passes the heating roller; and
a discarding roller configured to discard the film chip after the film chip on which the one or more polymerase chain reactions are performed passes the heating roller,
wherein the heating roller is configured to sequentially bring the heating blocks into contact with the film chip by a rotation of the heating roller and to induce gene amplification of the PCR sample present in the film chip.

2. The gene amplification apparatus of claim 1, wherein the plurality of heating blocks are disposed on an outer peripheral surface of the heating roller at regular intervals and are constantly maintained at different temperatures for denaturation, annealing, and extension, which are steps of PCR thermal cycling.

3. The gene amplification apparatus of claim 1, wherein the heating roller has a hollow shape and is made of a heat insulating material so that the plurality of heating blocks disposed on the circumferential surface thereof are maintained at different temperatures.

4. The gene amplification apparatus of claim 1, wherein the heating roller includes:
an external heating roller structure having a hollow shape and having a curvature corresponding to the heating block; and
a hole configured to communicate an inner space of the external heating roller structure with the outside.

5. The gene amplification apparatus of claim 4, wherein the plurality of heating blocks are disposed on a surface of the external heating roller structure so as to be maintained at different temperatures.

6. The gene amplification apparatus of claim 1, wherein the heating roller is disposed between the supply roller and the discarding roller so that one or more sections of the film chip in contact with the heating roller are pressed against the heating roller with a step difference.

7. The gene amplification apparatus of claim 1, wherein the gene amplification apparatus is configured to temporarily stop the film chip while the film chip is being moved toward the discarding roller and fill a PCR chamber of the plurality of PCR chambers when the film chip is temporarily stopped.

8. The gene amplification apparatus of claim 7, further comprising a sealing mechanism configured to block the PCR chamber from outside air when the film chip is aligned with an upper contact surface of the heating roller.

9. The gene amplification apparatus of claim 7, wherein:
a connection channel and a sample inlet form one conduit so that the PCR chamber is filled with the PCR sample; and
when the PCR chamber is filled with the PCR sample using the connection channel through the sample inlet, a separate elastically deformable body blocks the sample inlet from the outside air.

10. The gene amplification apparatus of claim 1, wherein the film chip is formed by laminating a plurality of films manufactured with a pattern.

* * * * *